(12) United States Patent
Young et al.

(10) Patent No.: US 7,318,832 B2
(45) Date of Patent: Jan. 15, 2008

(54) SURGICAL TOOL MECHANISM

(76) Inventors: Michael John Radley Young, Bremridge House, Bremridge, Ashburton, South Devon TQ13 7Jx (GB); Stephen Michael Radley Young, Bremridge House, Bremridge, Ashburton, South Devon TQ13 7JX (GB)

( * ) Notice: Subject to any disclaimer, the term of this patent is extended or adjusted under 35 U.S.C. 154(b) by 731 days.

(21) Appl. No.: 10/399,664

(22) PCT Filed: Oct. 17, 2001

(86) PCT No.: PCT/GB01/04632

§ 371 (c)(1), (2), (4) Date: Jun. 12, 2003

(87) PCT Pub. No.: WO02/38057

PCT Pub. Date: May 16, 2002

(65) Prior Publication Data
US 2004/0044356 A1 Mar. 4, 2004

(30) Foreign Application Priority Data
Oct. 17, 2000 (GB) .................................. 0025427.6

(51) Int. Cl.
*A61B 17/32* (2006.01)

(52) U.S. Cl. ...................................... 606/208; 606/169
(58) Field of Classification Search ................ 606/167, 606/169, 187, 174, 51, 52, 205–209; 601/2; 227/176.1, 175; 600/104
See application file for complete search history.

(56) References Cited

U.S. PATENT DOCUMENTS

| 5,669,544 A | * | 9/1997 | Schulze et al. | .......... 227/176.1 |
| 6,488,196 B1 | * | 12/2002 | Fenton, Jr. | ................ 227/175.1 |
| 2005/0216045 A1 | * | 9/2005 | Young et al. | ................ 606/169 |

* cited by examiner

*Primary Examiner*—(Jackie) Tan-Uyen Ho
*Assistant Examiner*—Melissa Ryckman
(74) *Attorney, Agent, or Firm*—Jeff Rothenberg, Esq.; Heslin Rothenberg Farley & Mesiti, P.C.

(57) ABSTRACT

The mechanism is applicable to a surgical tool which has a jaw (57) pivotably mounted to a distal end of a longitudinally extending support (58). The jaw is operated by action on a rearwardly facing cam follower (52, 53) by a lobe (51) on the distal end of an actuating tube (50). Rotation of the actuating tube (50) causes pivoting of the jaw (57) into and out of operative relationship with another jaw member (21) of the tool. The mechanism may be applied to any manipulative or gripping type of surgical implement, but is particularly applicable to ultrasonic tools adapted for cutting and/or coagulating.

19 Claims, 9 Drawing Sheets

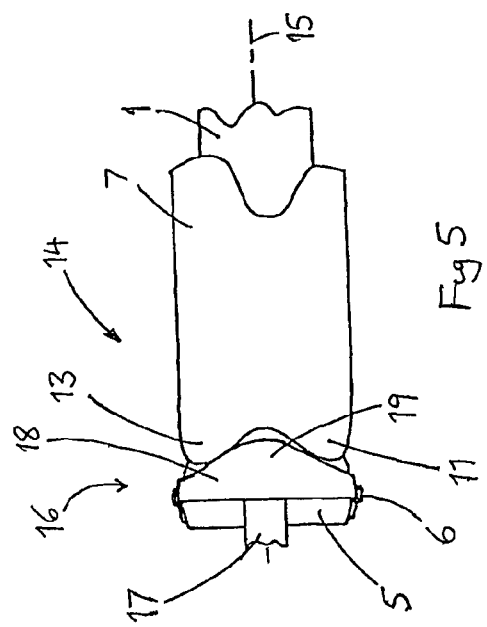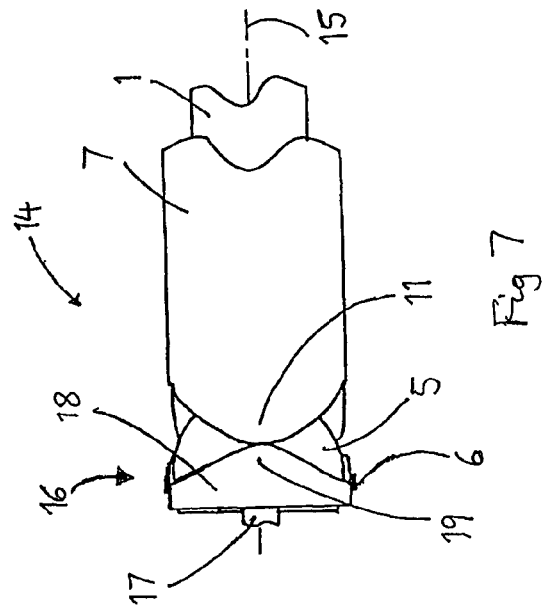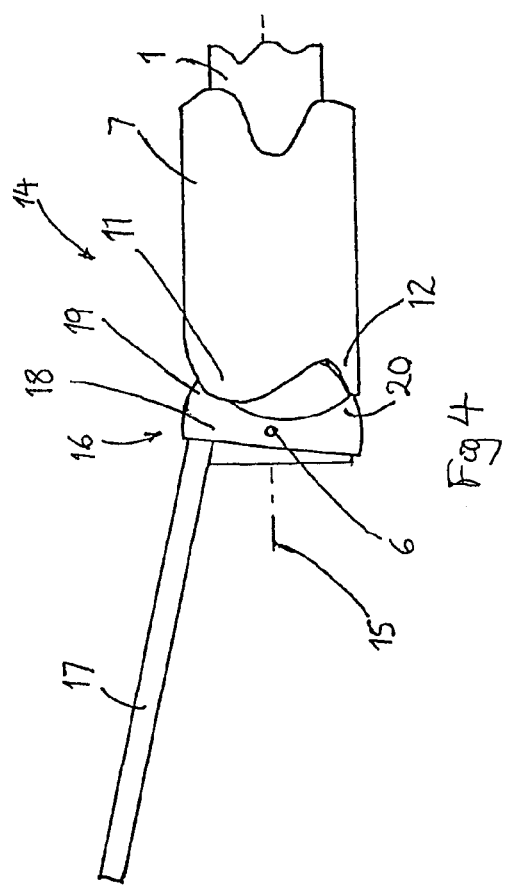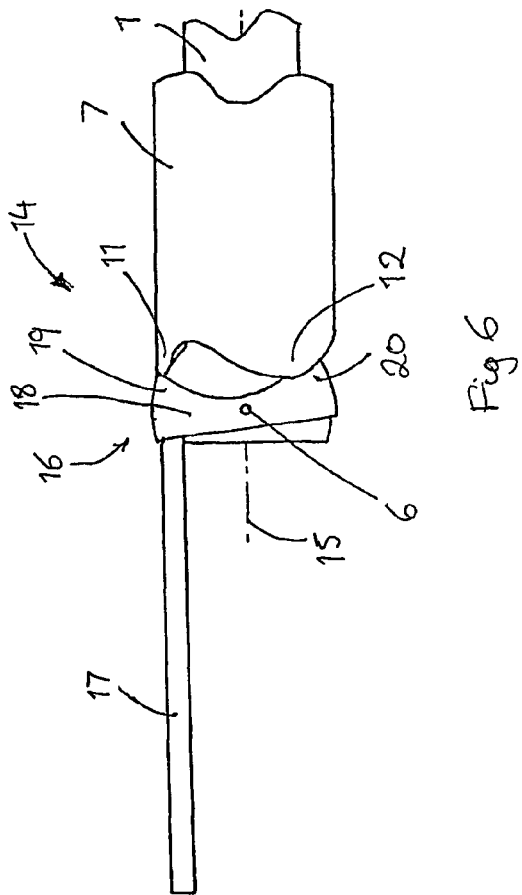

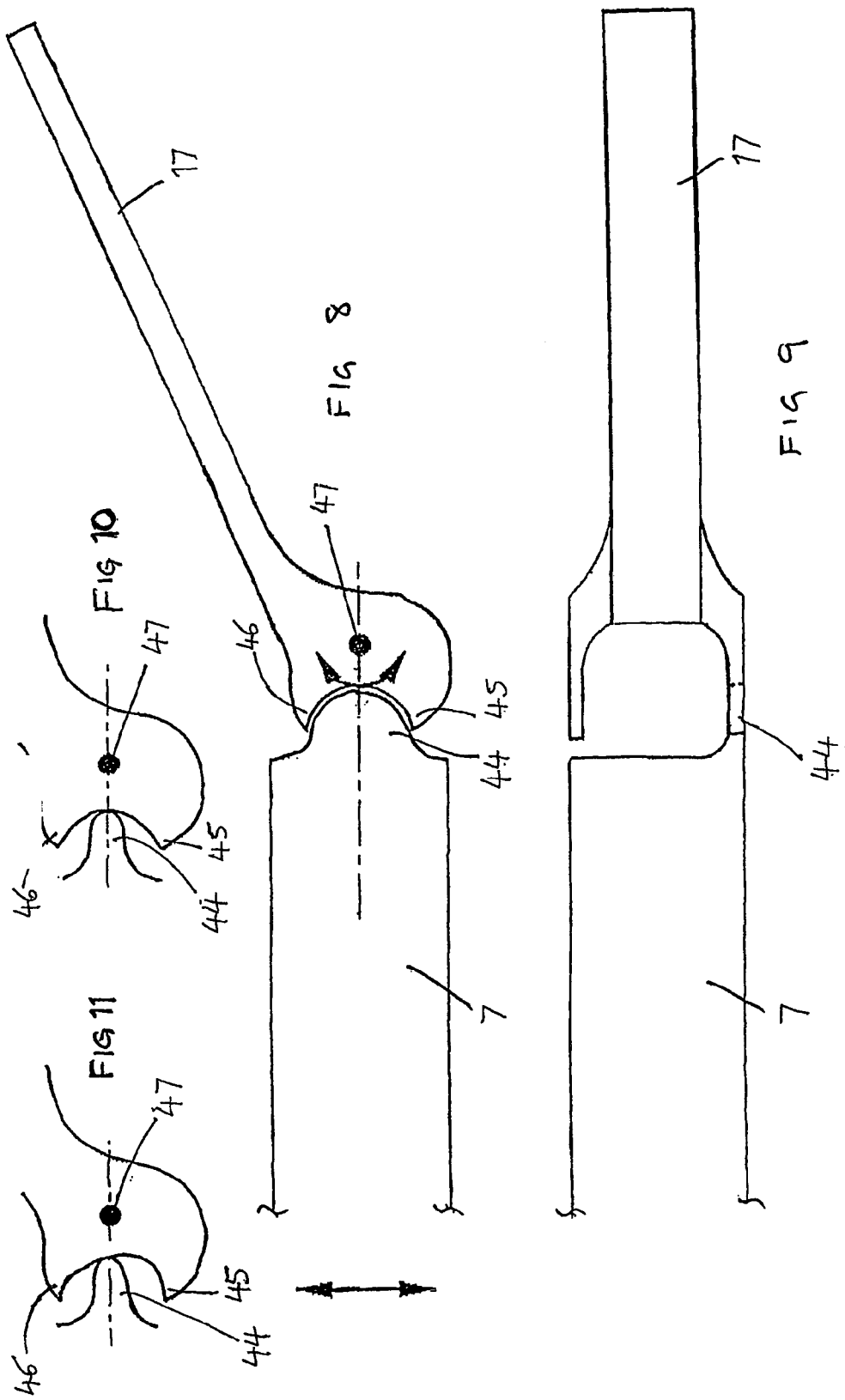

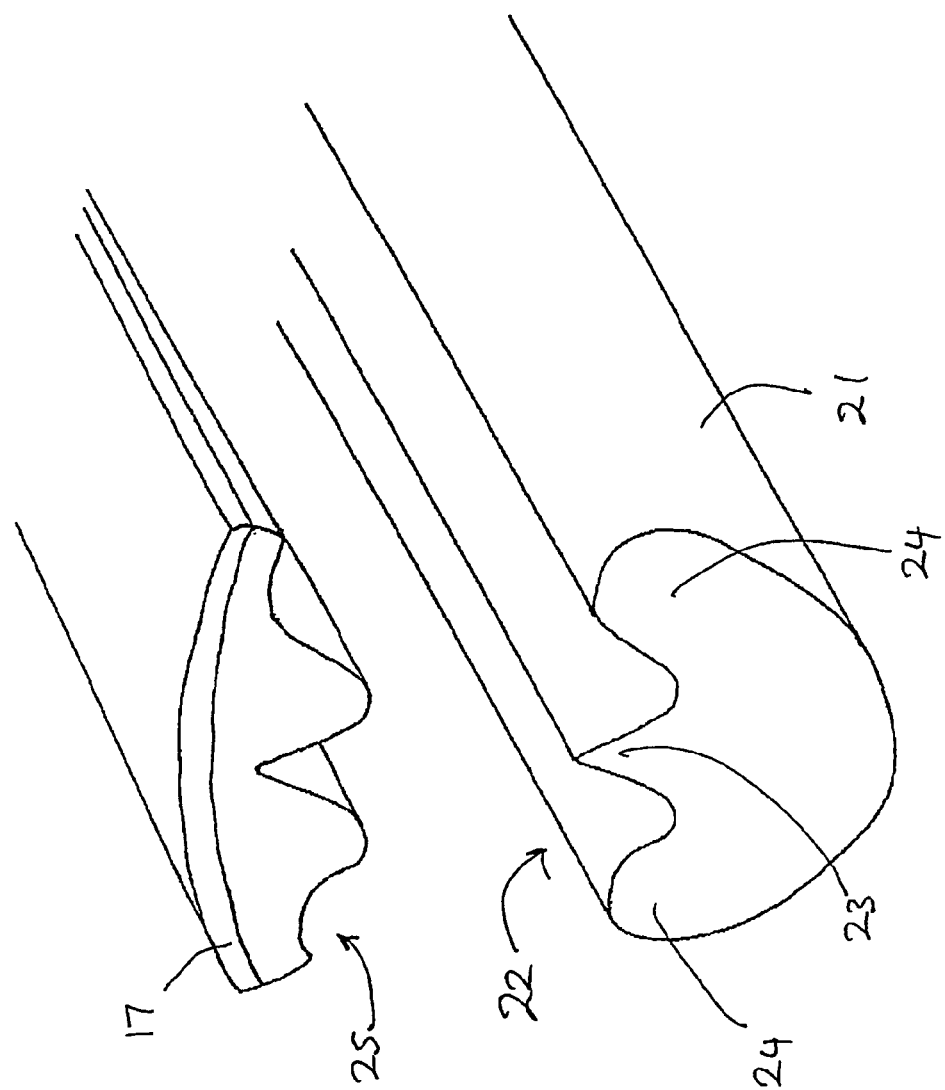

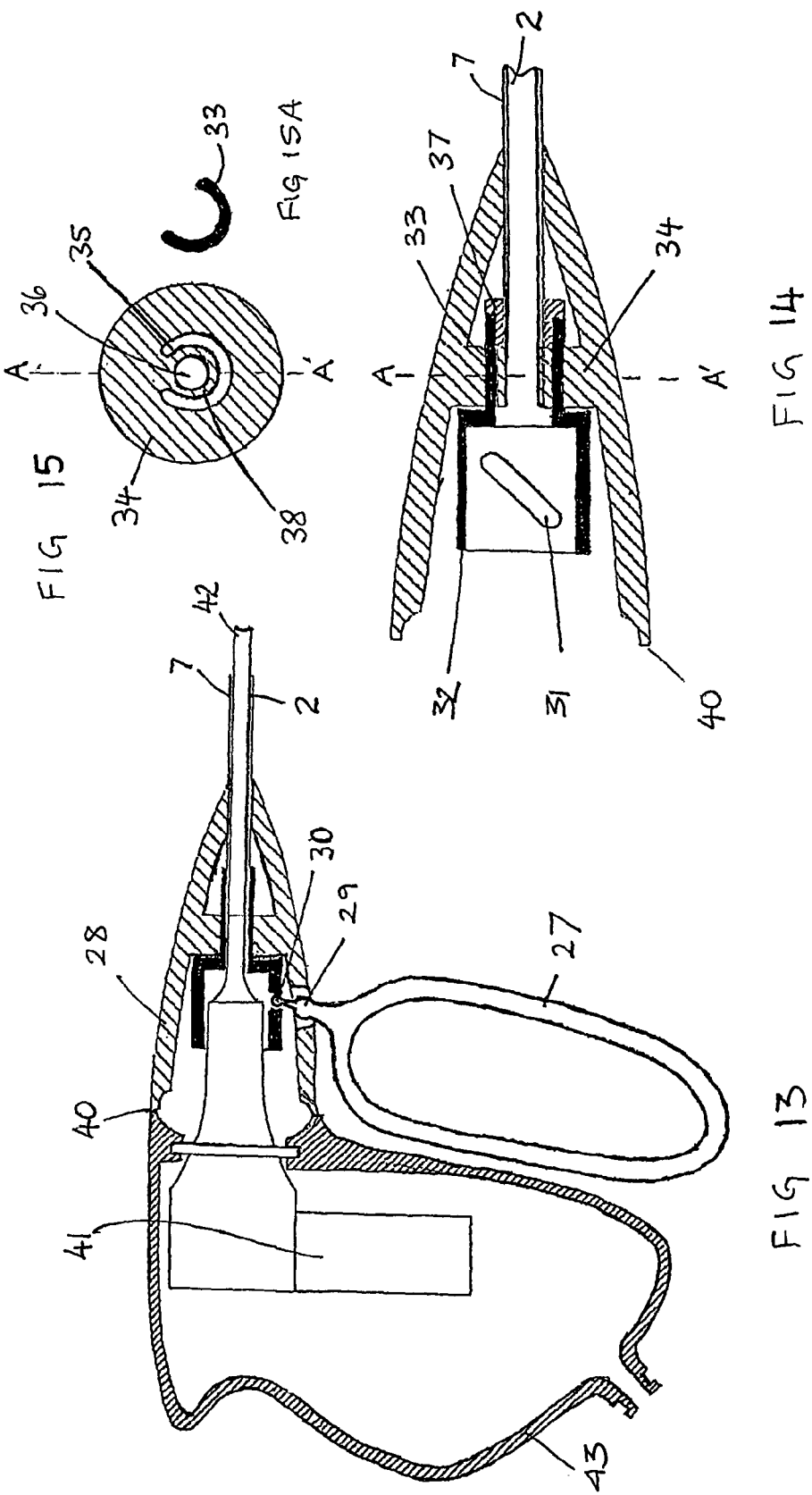

SURGICAL TOOL MECHANISM

The present invention relates to a surgical tool, and to a mechanism for its operation. More particularly, but not exclusively, it relates to an improved mechanism for operating an ultrasonic cutting and coagulating tool.

The mechanism is applicable to any surgical tool, particularly a laparoscopic tool where the surgeon may use a scissors-type, a pistol or trigger type grip outside the body to operate a manipulative, gripping or clamping mechanism at a distal end of the tool within the body. It is particularly, but not exclusively, useful for use with ultrasonically operated haemostatic cutting tools.

The invention will be described herein, for convenience, with respect to a preferred use with a haemostatic cutting tool, but its use is not limited thereto.

Such haemostatic cutting tools are known from British Patent Number 2333709B, International Patent Applications Numbers PCT/GB99/00162 and PCT/GB00/01580, and U.S. Pat. No. 5,322,055.

Each of the above identified patents and patent applications describes a surgical tool comprising means to generate ultrasonic vibrations and a waveguide, operatively connected at a proximal end to said generating means, and provided at a distal end with cutting and/or coagulating means. Each tool is provided with a jaw to hold tissue to be treated in contact with the ultrasonically vibrating cutting and/or coagulating means.

While several different actuating mechanisms have been employed to operate said jaw, they all amount to a reciprocable actuating member pushing or pulling on a part of the jaw to move it about a pivot, the actuating member being controlled by manual movements of a user of the tool. This has been found not to give sufficiently precise and subtle control over the movement of the jaw. These mechanisms focus very much on being able to clamp tissue hard against the cutting and/or coagulating means, rather than achieving any delicacy in handling soft tissues.

It is therefore an object of the present invention to provide an ultrasonic surgical tool, comprising a jaw and an ultrasonically active cutting and/or coagulating means, wherein the motion of the jaw relative to the cutting and/or coagulating means may be accurately and precisely controlled.

According to the present invention, there is provided a surgical tool comprising a longitudinally extending support means defining a longitudinal axis of said tool, an elongate centre member having a first jaw member at a distal end thereof, a longitudinally extending actuating means rotatable about said longitudinal axis, a second jaw member pivotably mounted to a distal end of said support means, and operating means for said second jaw member including rearwardly facing cam follower means, wherein a distal end of the actuating means is adapted to bear on said cam follower means, and is so configured that rotation of said actuating means causes pivoting of said second jaw member into and out of operative relationship with said first jaw member Preferably, the actuating means comprises an actuating tube concentrically surrounding said waveguide and said support means.

Preferably, said distal end of the actuating tube has an undulating profile with at least one lobe disposed to bear on the opposing surface of the operating means.

Said distal end of the actuating tube may be provided with an odd number of lobes, ideally three.

The two rearwardly facing cam follower protrusions may extend from diametrically opposed points of the operating means and be so disposed that the action of a lobe of the actuating tube on one said protrusion acts to pivot the jaw means into operative relationship with the cutting and/or coagulating means, and the action of a lobe on the other said protrusion acts to pivot the jaw means away from said operative relationship.

Optionally, said distal end of the actuating tube and the opposing surface of the operating means are configured to be co-operable to produce a smooth transition between successive dispositions of the jaw means.

The distal end of the actuating tube may be so configured that in a first orientation of said tube, one lobe is disposed to bear on a first protrusion of the collar means and the second said protrusion is disposed in a recess between lobes of the activating tube.

Said lobes and said protrusions may be so shaped as to co-operate to produce a controllable pivoting movement for a given rotational movement of the actuating tube.

In this case, said protrusions may be so spaced, with an intermediate curved zone between said protrusions, that the curved zone may cooperate with a lobe to move the jaw means between open and closed dispositions by a rotational movement of the lobe of between 20 and 60 degrees.

In an alternative embodiment, the distal end of the actuating tube may be provided with one actuating lobe.

In this case said protrusions may be so spaced, with an intermediate curved zone between said protrusions, that the curved zone may cooperate with said one lobe to move the jaw means between open and closed dispositions by a rotational movement of the lobe of between 60 and 180 degrees, preferably between 90 and 150 degrees, optionally in the region of 120 degrees.

The curved zone may be so shaped that the jaw means is caused to move comparatively slowly over a part of its travel and comparatively fast over another part of its travel.

The comparatively slow part of the travel of the jaw means may define a coagulation step.

The comparatively fast part of the travel of the jaw means may define a cutting step.

In another embodiment, there may be only a single protrusion acted upon by two lobes, there being an interlobal zone of such curvature as to control the movement of the jaw means between open and closed dispositions by a rotational movement of the lobes of between 90 and 120 degrees, preferably about 120 degrees.

The actuating tube may be operatively connected to a manually operated control means.

The control means may include means to ensure substantially continuous contact between the lobe or lobes and the operating or collar means, whatever the rotational disposition.

Advantageously, said manually operable control means comprises a trigger type mechanism or a scissors-like mechanism.

Such a trigger-type mechanism may be so mounted pivotably to a housing that it engages in a part helical slot of a turning means integral with or operatively associated with said actuating tube, whereby longitudinal movement of the trigger means causes rotation of the turning means and the actuating tube.

The turning means may be journalled by means of a part cylindrical extension member engaging in a part cylindrical slot, said slot being defined within bulkhead means of said housing between the main body thereof and a peninsular inner annulus thereof, said annulus being connected to the support means.

Preferably, said cutting and/or coagulating means has a profile adapted to cut, separate and/or coagulate tissue, as appropriate to the purpose of the tool, and the jaw means comprises a surface facing said cutting and/or coagulating means which has a complementary shape thereto.

Preferably, the distal end of said support means, is outwardly shaped as a portion of a sphere.

The operating means may be so complementarily shaped that said spherical portion may act as a guide to the movement thereof.

The tool may comprise a means of generating ultrasonic vibrations and a wave guide operatively connected thereto at a proximal end of the tool and provided at a distal end with cutting and/or coagulating means.

In a preferred embodiment, the means of generating ultrasonic vibrations is adapted to generate torsional mode ultrasonic vibrations.

Alternatively, the means of generating ultrasonic vibrations is adapted to generate longitudinal mode ultrasonic vibrations.

Embodiments of the present invention will now be more particularly described by way of example, and with reference to the accompanying drawings, in which:

FIG. 4 is an elevation of a distal end of a jaw mechanism in open condition, with the jaw disposed away from the longitudinal axis of the tool;

FIG. 5 is a plan view of the jaw mechanism of FIG. 4;

FIG. 6 is an elevation of the jaw mechanism in closed condition, with the jaw disposed towards the longitudinal axis of the tool;

FIG. 7 is a plan view of the jaw mechanism of FIG. 6;

FIG. 8 is an elevation of a distal end of another embodiment of jaw mechanism in open condition;

FIG. 9 is a plan view of the jaw mechanism of FIG. 8;

FIG. 10 is a scrap view of a possible contact area between the actuating tube and the operating collar;

FIG. 11 is a scrap view of a further possible contact area between the actuating tube and the operating collar;

FIG. 12 is a scrap perspective view of one possible jaw member and a cutting and coagulating tool particularly suitable for use with the present invention;

FIG. 13 is a longitudinal section through a proximal end of the tool;

FIG. 14 is a plan view of a proximal end housing with the generator and waveguide removed;

FIGS. 15 and 15A are a cross-section taken along the line A-A' of FIG. 14 with the turning element shown separately in FIG. 15A for clarity;

Figure 1:
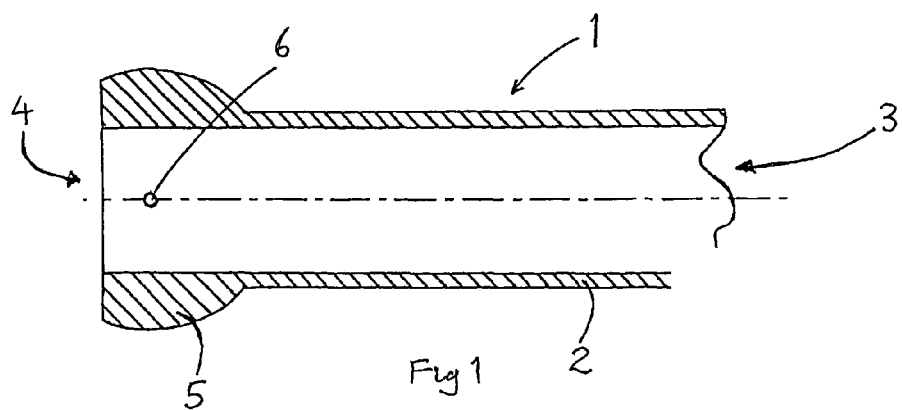
FIG. 1 is a cross-sectional view of a distal end of a support means of the tool.

Referring now to the drawings and to FIG. 1 in particular there is shown a support tube 1, which in this embodiment comprises an elongate hollow cylinder 2 dimensioned to accept a waveguide (not shown) for ultrasonic vibrations, or other elongate member. The support tube 1 is insulated from the ultrasonic vibrations by spacers (not shown) along its length. In the preferred embodiment, torsional mode ultrasonic vibration is used, but the tool could equally well utilise longitudinal mode vibrations.

The distal end 4 of the support tube 1 is provided with a thickening 5 of the cylinder wall, the outer surface of the thickening 5 comprising a portion of a spherical surface. Pivot points 6 are provided at diametrically opposed locations of the thickening 5 for pivotable attachment of a jaw assembly (not shown in this Figure).

Figure 2:
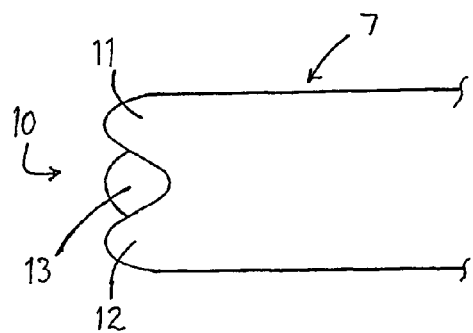
FIG. 2 is an elevation of a distal end of an actuating tube of the tool.
Figure 3A:
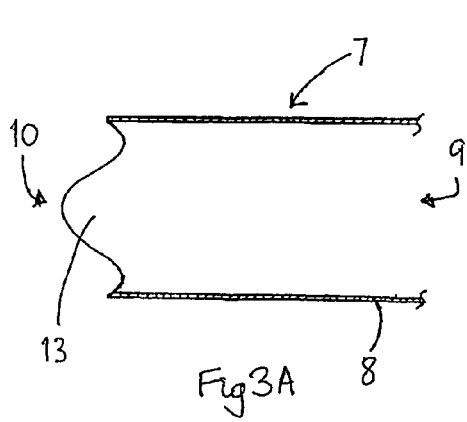
FIGS. 3A and 3B are cross-sectional views of the distal end of the actuating tube of FIG. 2.
Figure 3B:
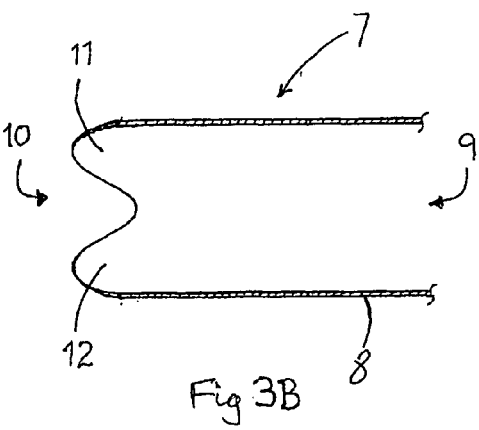

FIGS. 2, 3A and 3B show an actuating tube 7, which comprises an elongate hollow cylinder 8 dimensioned to accept the cylinder 2 of the support tube 1. The actuating tube 7 is rotatable with respect to the support 1 under the control of manually operable trigger means at the proximal end of the tube 7, and a distal end 10 of the actuating tube 7 bears three symmetrically-disposed lobes 11, 12, 13.

A jaw mechanism 14 and its operating components are shown in FIGS. 4 to 7. The fixed and active part of the jaw mechanism comprises the distal end of the waveguide terminating in a shaped cutting and coagulating member which is located along the longitudinal axis 15 of the tool.

A movable and passive part of the mechanism comprises a jaw assembly 16 in which a jaw arm 17 is mounted, away from a longitudinal axis 15 of the tool, to an operating collar 18, which is itself mounted to the support tube 1 at diametrically opposed pivot points 6, so it can oscillate or rock between two end points. The collar 18 is shaped internally to correspond to a portion of the surface of the spherical thickening 5 Of the support tube 1. The collar 18 bears two rearwardly or proximally facing cam follower protrusions 19, 20, arranged at one hundred and eighty degrees separation and each at ninety degrees to the pivot points 6, and adapted to coact with the lobes 11, 12 and 13 and with the interlobal spaces of the actuating tube 7.

In the disposition shown in FIGS. 4 and 5, the second lobe 12 of the actuating tube 7 is bearing on a second protrusion 20 of the collar 18, urging the adjacent part of the collar 18 distally, and thereby rocking the jaw assembly 16 about the pivot points 6 such that the jaw arm 17 is angled away from the longitudinal axis 15. As is clear from FIG. 5, a first protrusion 19 is disposed between the first and third lobes 11, 13 of the actuating tube 7.

When the actuating tube 7 is rotated in a clockwise sense by approximately 60°, the disposition shown in FIGS. 6 and 7 is achieved. The first lobe 11 of the actuating tube 7 engages with the first protrusion 19 of the collar 18, and thereby displaces the adjacent portion of the collar 18 distally. The jaw assembly 16 thus rocks about the pivot points 6, such that the jaw arm 17 approaches the longitudinal axis 15. The forms of the cutting and coagulating tool disposed along the axis 15 and a contact surface attached to the jaw arm 17 are such that they are in contact, or close thereto, in this disposition.

The lobe 12 of the actuating tube 7 has moved clear of the second protrusion 20 of the collar 18, which now lies between the second and third lobes 12, 13.

When the actuating tube 7 is then rotated in an anticlockwise sense by approximately 60°, the disposition shown in FIGS. 4 and 5 is regained, and the jaw arm 17 is angled away in an "open" position.

In an alternative operating system, the actuating tube 7 may be further rotated in the same clockwise sense. Such action would move the first lobe 11 clear of the first protrusion 19, and the third lobe 13 will bear on the second protrusion 20, pivoting the jaw assembly 16 back towards the "open" disposition as shown in FIGS. 4 and 5.

Obviously, given that there are three equiangularly spaced lobes, any rotation of the actuating tube through 60° in either a clockwise or an anticlockwise sense will rock the collar from one end position to the other and thereby either close or open the jaw.

As can be seen, the exact rate of pivotal movement of the jaw assembly 16 depends not only on the rate of rotation of the actuating tube 7, but also on the profile of the lobes 11, 12, 13. Suitable choices of this profile can produce relatively slow and controlled movement when close to the disposition of FIGS. 4 and 5, at which point soft tissue may be gripped between the jaw and the cutting and coagulating tool. More rapid movement is preferable when close to the disposition shown in FIGS. 6 and 7, when the jaw is about to cut the vessel, having already coagulated the areas either side of the proposed cut. It is advantageous to have a longer dwell time during the coagulation phase, followed by a short sharp cutting phase.

An alternative embodiment of jaw assembly is shown in FIGS. 8 to 10. In this case, a single lobe 44 of the actuating tube 7 is adapted to act on a collar having two protrusions 45 and 46 separated by an angle no more than 180°. Indeed, the spacing of the protrusions 45 and 46 may be such that the actuating tube 7 need only rotate through as little as 20° for it to act on the collar to move the jaw from open to closed or vice versa. The preferred degree of rotation is between 25° and 35°. This arrangement is shown in FIGS. 8 and 9 where the single lobe 44 so acts on the protrusion 45 that the jaw is open at approximately 45° to the longitudinal axis 15 and it can be moved rotationally to contact protrusion 46 where the jaw is pivoted about point 47 to be closed.

However, the curved surface of the collar between the protrusions may be shaped to determine the speed of contact between the elements of the jaw and the force applied to the jaw movement. FIG. 8 shows a straightforward circular contact area where rotation of the actuating tube 7 will effect a substantially linear correlation between rotation and jaw movement. That is to say, at the mid point of the rotational movement of the actuating tube 7, the jaw member 17 is midway between open and closed—at 22.5° to the longitudinal axis. This symmetry may be varied, as may be seen in FIGS. 10 and 11. In FIG. 10, the collar has a parabolic curve, which gives a longer dwell time at an intermediate point in the coming together of the jaw members.

FIG. 11 shows a preferred arrangement in which the lobe 44 at first contacts protrusion 45 with the jaw 17 at approximately 45° to the longitudinal axis. Rotational movement of the lobe 44 then causes rapid movement of the collar so that the jaw is at approximately 22.5° to the longitudinal axis 15. After that, the collar's surface is so curved that the jaw closes only very slowly during a coagulation phase until a final sharp closure caused by the protrusion 46.

Thus, coagulation of a blood vessel can be accomplished comparatively gradually, on either side of a projected cutting point, until suddenly and quickly—the cut is then made. The system then retracts to a more relaxed form of release. The surgeon does not have to concern himself with differential pressure at the handgrip since a simple pull on the trigger will cause variable preselected degrees of pressure at the workplace.

As can be seen from FIG. 12, the jaw 17 is shaped to cooperate with a static first jaw member or anvil 21, which in this case is ultrasonically vibrated. This anvil 21 comprises a comparatively sharp central ridge 23 and, on either side thereon, comparatively rounded coagulating edges 24.

Referring now to FIGS. 13 to 15, there is shown a preferred form of manual operation for the tool. A trigger-type handle 27 is mounted to a proximal end housing 28 at a pivot point 29 adjacent an opening in the wall of the housing 28. The handle 27 extends beyond the pivot point 29 connected to a pin 30 which is engaged in a part-helical slot 31 in a turning element 32. The cylindrical turning element 32 is supported for rotation by means of a part-cylindrical extension 33 thereof which is adapted to co-act in a part-cylindrical slot 35 in a bulkhead 34 of the housing 28. The bulkhead also has a central aperture 36 to accommodate the waveguide 42.

The extension 33 of the turning element is connected at 37 to the outer actuating tube 7, while the inner support tube 2 is connected directly to the bulkhead 34 at a part-isolated portion 38, separated from the main body thereof by the part cylindrical slot 35. The part cylindrical slot 35 between the inner portion 38 and the main body of the bulkhead 34 is dimensioned to allow the part-cylindrical extension 33 to move rotationally through an angle of up to sixty degrees from one end to the other of the slot 35. As stated above, in some embodiments, the actuating tube 7 needs to move through 60°, while in others the rotation may be as little as 20°, in which case the slot may be shorter.

Movement of the trigger 27 causes the pin 30 to move within the part-helical slot 31, generally from one end towards the other, thereby turning the turning element 32 and the actuating tube 7, with effects at the distal end as described above. Obviously, the return movement of the trigger 27 reverses the rotational movement of the actuating tube 7.

The housing 28 and the sleeves 2 and 7 may be disconnected at point 40 from the ultrasonic vibration generator 41, its housing 43 and the waveguide 42 so that they may be discarded after each use, if so desired.

A variety of configurations of jaw and cutting and coagulating tool are suitable for use in conjunction with the jaw mechanism of the present invention, some of which are described in our British Patent Number 2333709B. One particular form, preferred herein, will be described in more detail with reference to FIG. 12.

An end of the waveguide is configured as a cutting and/or coagulating tool 21 which has an operating surface 22 having a profile which comprises a central acutely-angled cutting element 23, flanked by two relatively rounded coagulating elements 24.

The jaw arm 17 has a contact surface 25 which has a complementary shape to that of the operating surface 22.

The contact surface 25 may be brought down towards the operating surface 22 by operation of the jaw mechanism described above, such that soft tissue, for example a blood vessel, may be held between the surfaces 22, 25. Transmission of torsional mode ultrasonic vibrations to the tool 21 causes the element 23 to act against the corresponding part of the contact surface 25 to sever the blood vessel, while the rounded elements 24 act against the contact surface 25, coagulating the tissue and sealing the blood vessel on either side of the point at which the element 23 is severing it.

As has been described above, the arrangements shown in FIGS. 8 to 11 enable the two surfaces 22, 25 to be brought together in a controlled manner, to avoid damaging the blood vessel before it can be sealed. The jaw mechanism described in relation to FIG. 11 shows that the operating collar may be so shaped as to cause a comparatively long period of coagulation while the two surfaces are slowly brought towards one another and a short period of cutting when the two surfaces are in contact.

Figure 16:
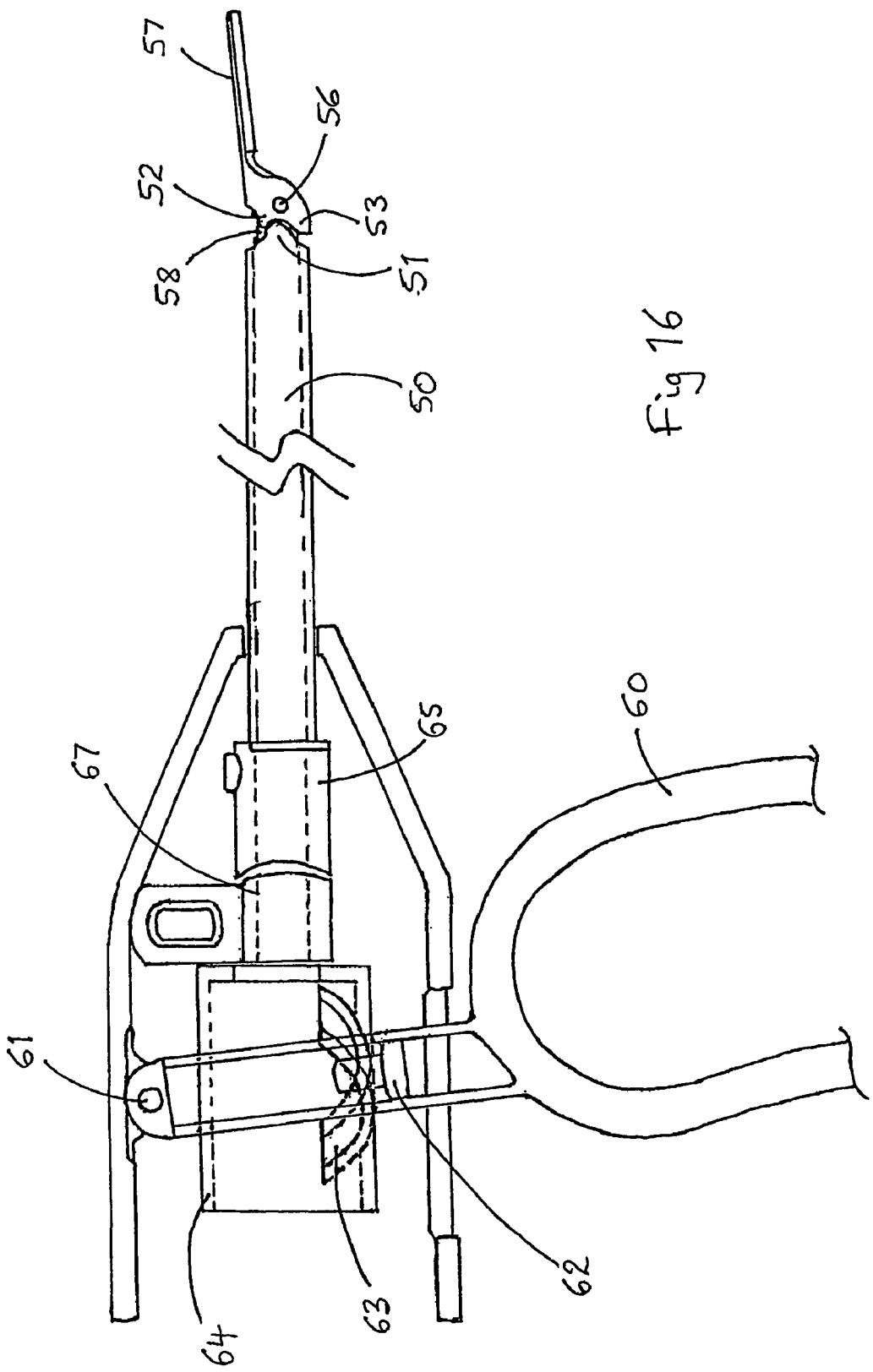
FIG. 16 is a schematic longitudinal section of a preferred embodiment of the tool.

Referring now to FIG. 16, there is shown a preferred embodiment of the invention in which the actuating tube is provided with only a single lobe. The single lobe 51, integral with actuating tube or sleeve 50, can act on either one of two rearwardly facing cam following protrusions 52 and 53, to operate the second jaw member 57. This is pivoted about point 56 to an end member 58 of the support tube.

Figure 17A:
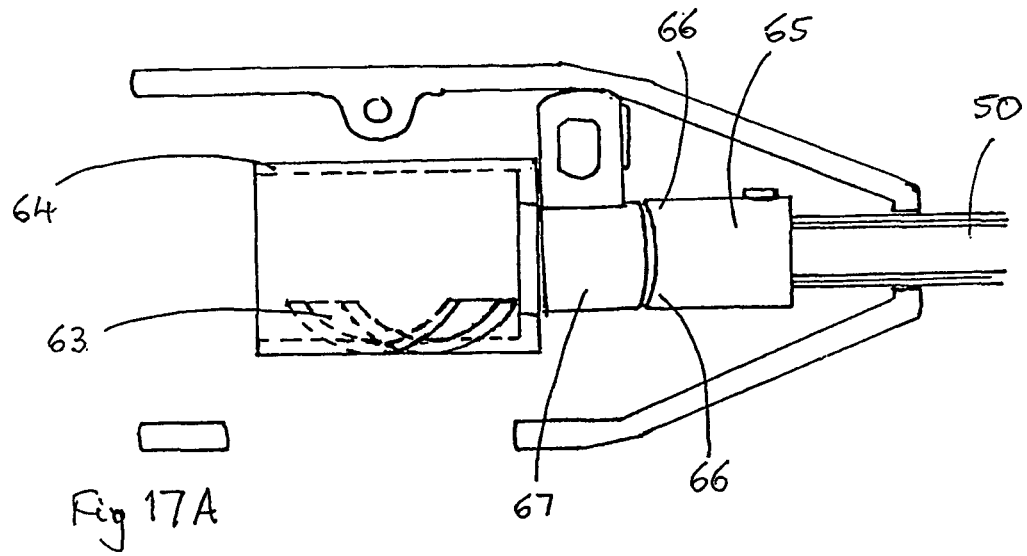
FIG. 17A is a scrap elevation of a turning member of the tool of FIG. 16 when the jaw member is in an intermediate disposition.
Figure 17B:
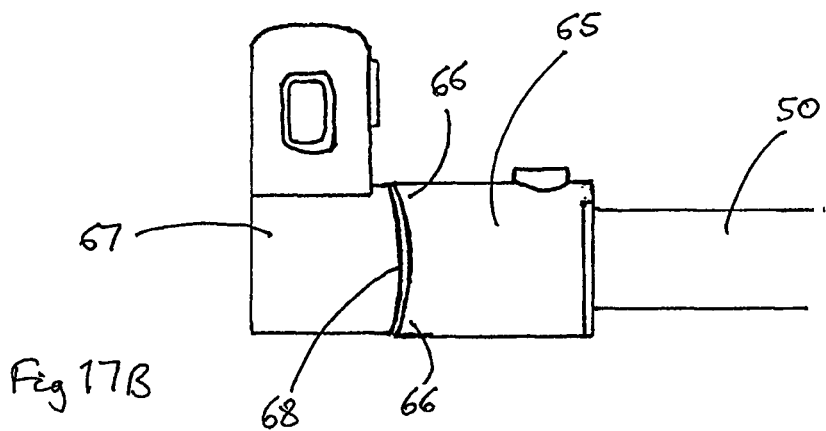
FIG. 17B is a scrap elevation of a compensating cam arrangement when the jaw member is in an intermediate disposition.
Figure 17C:
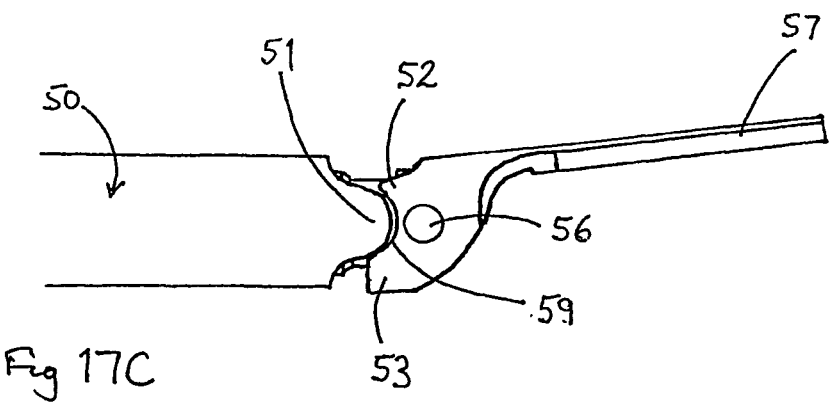
FIG. 17C is a scrap elevation of a distal end of the tool of FIG. 16 when the jaw member is in an intermediate disposition.
Figure 18A:
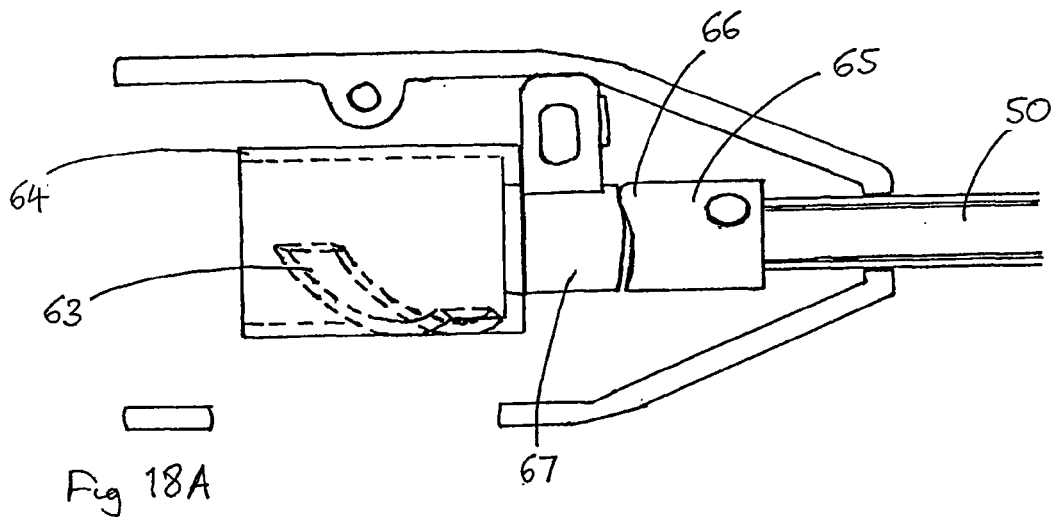
FIG. 18A is a scrap elevation of a turning member of the tool of FIG. 16 when the jaw member is in an open disposition.
Figure 18B:
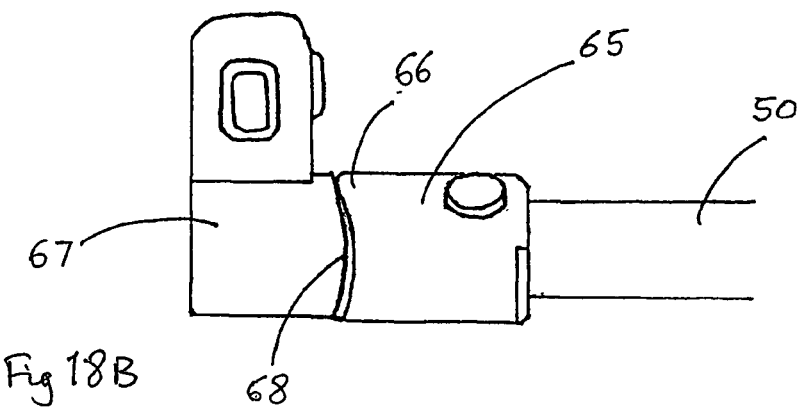
FIG. 18B is a scrap elevation of a compensating cam arrangement when the jaw member is in an open disposition.
Figure 18C:
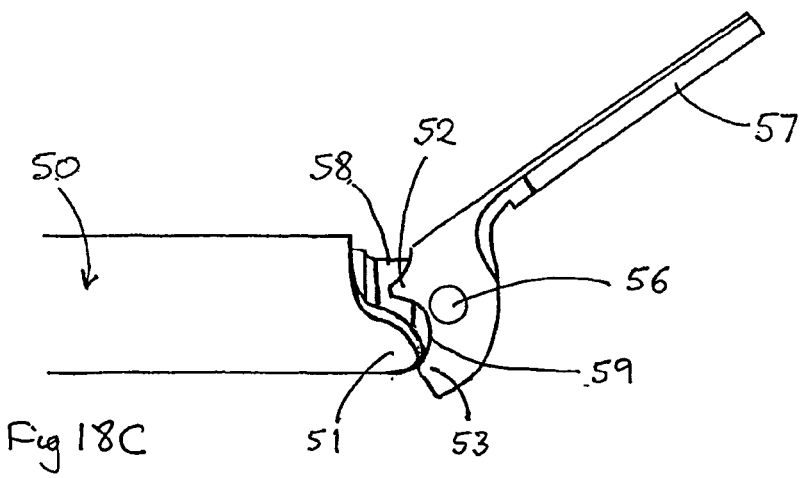
FIG. 18C is a scrap elevation of a distal end of the tool of FIG. 16 when the jaw member is in an open disposition.
Figure 19A:
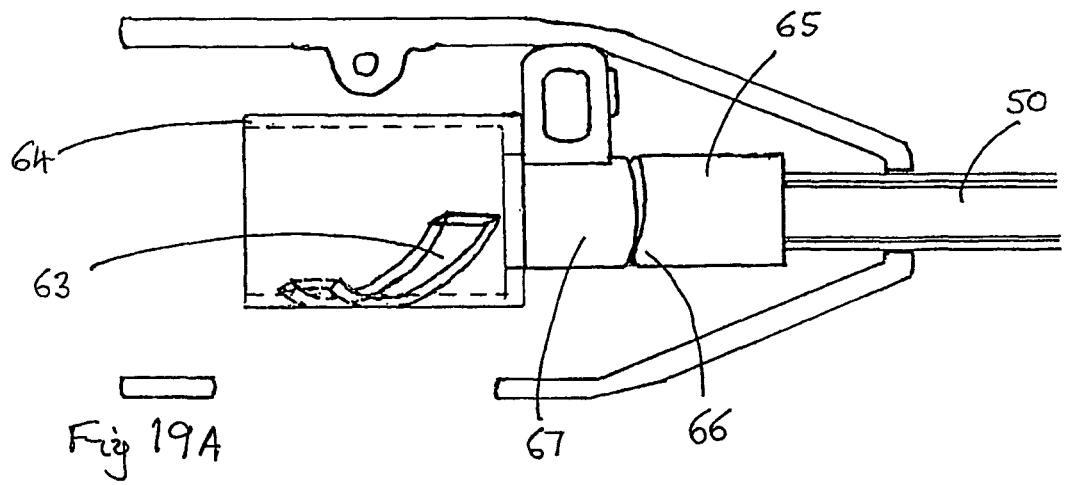
FIG. 19A is a scrap elevation of a turning member of the tool of FIG. 16 when the jaw member is in a closed disposition.
Figure 19B:
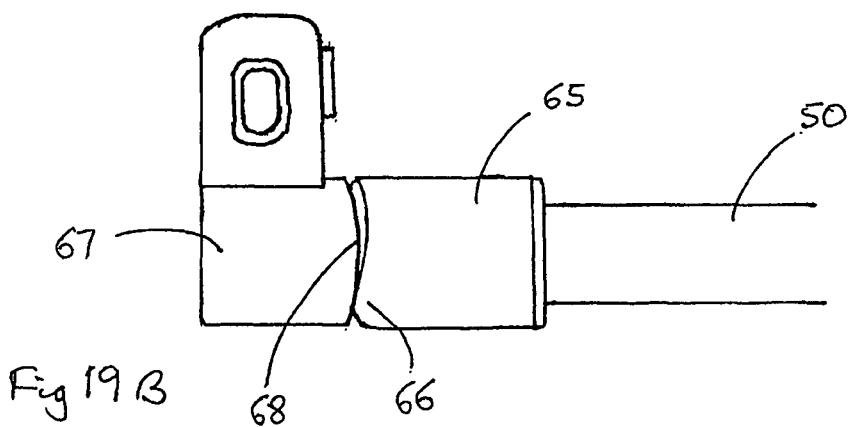
FIG. 19B is a scrap elevation of a compensating cam arrangement when the jaw member is in a closed disposition.
Figure 19C:
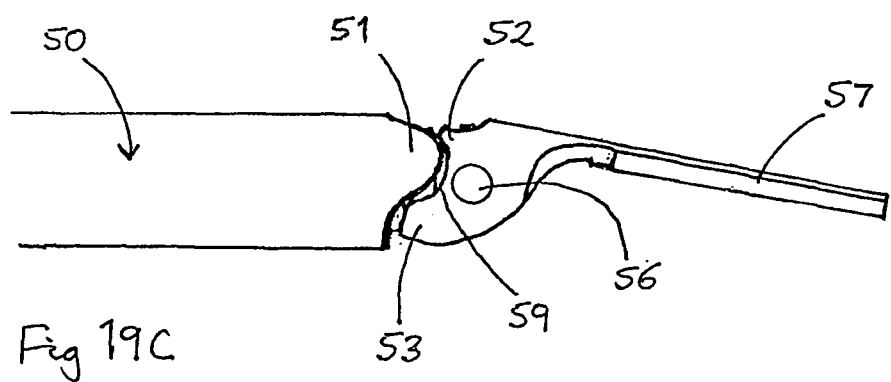
FIG. 19C is a scrap elevation of a distal end of the tool of FIG. 16 when the jaw member is in a closed disposition.

Referring now to FIGS. 17C, 18C and 19C, it can be seen that the lobe 51 at the intermediate position shown in FIG. 17C lies in contact with the curved surface 59 separating the protrusions 52 and 53. For clarity of illustration of the drawings, a small gap is indicated between the lobe 51 and the surface 59. In fact, it is important that the lobe 51 remains in contact with the surface 59 at all times.

As can be seen from FIG. 18C, clockwise (looking from the proximal to the distal end) rotation of the actuating tube 50 causes the lobe 51 to contact protrusion 53 causing the jaw 57 to pivot about point 56 into an open position.

Similarly, as shown in FIG. 19C, anti-clockwise rotation of the actuating sleeve 50 causes the lobe 51 to contact the other protrusion 52 and pivot the jaw 57 into a closed disposition.

In these three drawings referred to above, a first jaw member or anvil is not shown, since this may take any one of several forms which are not relevant to the operation of the second jaw 57.

Rotation of the actuating tube 50 is achieved by movement of a trigger 60 which is so pivoted about a pivot point 61 that a proximally directed pull on the trigger 60 will cause anti-clockwise rotation of tube 50, thereby closing the jaw 57 while a distally directed push on the trigger 60 will cause clockwise rotation of the tube 50 and open the jaw 37. This rotation is achieved by means of an actuating screw 62 engaging in a part helical slot 63 in a rotatable barrel 64. The slot 63 extends around approximately 120 degrees of the circumference of the barrel 64.

As can be seen from FIGS. 17A, 18A and 19A, a pivoting movement of the actuating screw (not shown in these figures) caused by longitudinal movement of the trigger 60 causes the barrel 64 to rotate as shown. The barrel 64 is connected to the actuating tube 50 for rotation, but the actuating tube 50 is capable of a small degree of longitudinal movement with respect to the barrel 64 as described below.

As stated above, it is important for smooth operation of the tool that the lobe 51 remains in contact with the curved surface 59 and/or the protrusions 52 and 53 at all times. Given that the lobe 51 and the curved surface 59 are both additionally curved about the axis of the tube 50, the locus of the point of contact between them is a gentle curve of amplitude between 0.25 and 1 mm, and that jaw member 57 is pivoted about a point 56 spaced from the point of action of the lobe 51, this cannot be achieved by straightforward rotation of the activating tube 50. Accordingly, there is provided a compensating cam collar 65 at a proximal end of the actuating tube 50. This has a rearwardly facing pair of cam followers 66 and is shown in more detail in FIGS. 17B, 18B and 19B. The actuating tube 50, connected for rotation to the barrel 64, passes through a cylindrical aperture in a fixed member 67. The fixed member 67 has a distally facing cam surface 68, and the degree of curvature between the cam surface 68 and the cam followers 66 of the collar 65 is such that longitudinal movement of the actuating tube 50 of between 0.25 and 1 mm may be achieved between each rotational end position and the intermediate position of the actuating tube 50.

At an intermediate position, as shown in FIG. 17B, there is in fact, no gap between surfaces 66 and 68 (although one is shown for the purpose of clarity). As the actuating tube 50 is rotated by rotation of the barrel 64, the collar 65 which is fixed to the tube 50 causes either one of the cam followers 66 to contact the fixed curved surface 68 and urge the actuating tube 50 distally. This ensures that the lobe 51 at the distal end of the actuating tube 50 remains in contact with either of the protrusions 52 or 53 during the final stages of opening or closing the jaw 57. This ensures smooth operation of the jaw 57 without sticking in any position.

The invention claimed is:

1. A surgical tool comprising a longitudinally extending support means defining a longitudinal axis of said tool, an elongate center member having a first jaw member at a distal end thereof, a longitudinally extending actuating means rotatable about said longitudinal axis, a second jaw member pivotably mounted to a distal end of said support means, and operating means for said second jaw member including rearwardly facing cam follower means, wherein a distal end of the actuating means is adapted to bear on said cam follower means, and is so configured that rotation of said actuating means causes pivoting of said second jaw member into and out of operative relationship with said first jaw member, and wherein the rearwardly facing cam follower means comprises two protrusions extending from substantially diametrically opposed points of the operating means and so disposed that action of a lobe at the distal end of the actuating means on one of said protrusions acts to pivot the second jaw member into operative relationship with the first jaw member, and action of a lobe on a second of said protrusions acts to pivot the jaw means away from said operative relationship.

2. A tool as claimed in claim 1, wherein the actuating means comprises an actuating tube concentrically surrounding said support means.

3. A tool as claimed in claim 2, wherein said distal end of the actuating means has an undulating profile with at least one lobe disposed to bear on an opposing surface of the operating means.

4. A tool as claimed in claim 3, wherein the distal end of the actuating tube is provided with three lobes.

5. A tool as claimed in claim 4, wherein the distal end of the actuating tube is so configured that in a first orientation of said tube one lobe is disposed to bear on a first protrusion of the operating means and the second said protrusion is disposed in a recess between other lobes of the activating tube.

6. A tool as claimed in claim 5, wherein the protrusions are so spaced and separated by an intermediate curved zone that the second jaw member moves between open and closed dispositions by a rotational movement of the lobe of between 20 and 60 degrees.

7. A tool a claimed in claim 1, wherein the distal end of the actuating tube is provided with a single lobe.

8. A tool as claimed in claim 7, wherein the protrusions are so spaced and separated by an intermediate curved zone that the second jaw member moves between open and closed dispositions by a rotational movement of the lobe of between 60 and 180 degrees.

9. A tool as claimed in claim 8, wherein the rotational movement is between 90 and 150 degrees, preferably in the region of 120 degrees.

10. A tool as claimed in claim 1, wherein the actuating means is operatively connected to a manually operable control means.

11. A tool as claimed in claim 10, wherein the control mechanism is so mounted pivotably to a housing that it engages in a part helical slot of a turning means integral with or operatively associated with said actuating means, whereby longitudinally directed movement of the control mechanism causes rotation of the turning means and the actuating means.

12. A tool as claimed in claim 11, further comprising compensation means so that during said rotational movement, longitudinal movement of the actuating means occurs, whereby the lobe remains always in contact with the rearwardly facing surface of the operating means.

13. A tool as claim in claim 1, further comprising means of generating ultrasonic vibrations and a waveguide operationally connected thereto at a proximal end.

14. A tool as claimed in claim 13, wherein the means of generating ultrasonic vibrations is adapted to generate ultrasonic vibrations in a torsional mode.

15. A tool as claimed in claim 13, wherein the waveguide is provided at its distal end with cutting and/or coagulating means.

16. A tool as claimed in claim 6, wherein the curved zone is so shaped that the jaw means is caused to move comparatively slowly over a part of its travel and comparatively fast over another part of its travel.

17. A tool as claimed in claim 16, wherein the comparatively slow part of the travel of the jaw means define a coagulation step.

18. A tool as claimed in claim 16, wherein the comparatively fast part of the travel of the jaw means defines a cutting step.

19. The tool as claimed in claim 10, wherein the control means comprises a trigger type mechanism.

\* \* \* \* \*

UNITED STATES PATENT AND TRADEMARK OFFICE
CERTIFICATE OF CORRECTION

PATENT NO. : 7,318,832 B2 Page 1 of 1
APPLICATION NO. : 10/399664
DATED : January 15, 2008
INVENTOR(S) : Young et al.

It is certified that error appears in the above-identified patent and that said Letters Patent is hereby corrected as shown below:

Claim 7, Col. 9, Line 1: Delete "A tool a claimed" and insert -- A tool as claimed --

Claim 13, Col. 10, Line 1: Delete "A tool as claim" and insert -- A tool as claimed --

Signed and Sealed this

Twentieth Day of May, 2008

JON W. DUDAS
*Director of the United States Patent and Trademark Office*